(12) United States Patent
Fostick et al.

(10) Patent No.: US 10,667,842 B2
(45) Date of Patent: Jun. 2, 2020

(54) PERICARDIAL NEEDLE MECHANISM

(71) Applicant: RAINBOW MEDICAL LTD., Herzliya (IL)

(72) Inventors: Gideon Fostick, Givat Shmuel (IL); Ilan Uchitel, Kfar-Saba (IL); Evgeni Venislavski, Rosh Haayin (IL); Michael Lis, Rishon Lezion (IL)

(73) Assignee: RAINBOW MEDICAL LTD., Herzliya (IL)

( * ) Notice: Subject to any disclaimer, the term of this patent is extended or adjusted under 35 U.S.C. 154(b) by 238 days.

(21) Appl. No.: 15/821,973

(22) Filed: Nov. 24, 2017

(65) Prior Publication Data

US 2019/0159808 A1 May 30, 2019

(51) Int. Cl.
*A61B 17/34* (2006.01)
*A61B 90/00* (2016.01)
(Continued)

(52) U.S. Cl.
CPC ...... *A61B 17/3476* (2013.01); *A61B 17/3403* (2013.01); *A61B 17/3478* (2013.01); *A61B 17/3496* (2013.01); *A61B 90/361* (2016.02); *A61B 2017/00022* (2013.01); *A61B 2017/00247* (2013.01); *A61B 2017/00561* (2013.01); *A61B 2017/00902* (2013.01);
(Continued)

(58) Field of Classification Search
CPC ...... A61B 2017/00623; A61B 17/0057; A61B 17/062–06052; A61B 1/00094; A61B 1/012; A61B 1/018; A61B 5/15186; A61B 5/15188–15198; A61B 17/3476; A61B 17/3478; A61B 17/3496; A61B 2017/3409; A61B 2017/3405; A61B 2017/3403
See application file for complete search history.

(56) References Cited

U.S. PATENT DOCUMENTS

| 5,309,896 A | 5/1994 | Moll et al. |
| 5,335,671 A | 8/1994 | Clement |
| (Continued) | | |

FOREIGN PATENT DOCUMENTS

| CN | 1628615 A | 6/2005 |
| DE | 10126062 | 12/2001 |
| (Continued) | | |

OTHER PUBLICATIONS

An Office Action dated Mar. 22, 2018, which issued during the prosecution of U.S. Appl. No. 14/324,457.
(Continued)

*Primary Examiner* — Katrina M Stransky
*Assistant Examiner* — Brigid K Byrd
(74) *Attorney, Agent, or Firm* — Sughrue Mion, PLLC

(57) ABSTRACT

Apparatus is provided including a surgical tool configured to be advanced distally within a body of a subject. The surgical tool is shaped to define a side-facing suction port at a distal portion of the surgical tool to facilitate drawing tissue through the suction port and into the surgical tool, and includes a slidable transparent shutter configured to be disposed over the suction port, and to be slidably removed from the suction port. A needle is configured to be slidably disposed within the surgical tool and configured to puncture the tissue while the tissue is in the surgical tool. Other applications are also described.

21 Claims, 10 Drawing Sheets

(51) Int. Cl.
*A61B 17/00* (2006.01)
*A61B 17/30* (2006.01)
(52) U.S. Cl.
CPC . *A61B 2017/306* (2013.01); *A61B 2017/3409* (2013.01); *A61B 2017/3488* (2013.01)

(56) References Cited

U.S. PATENT DOCUMENTS

| | | | |
|---|---|---|---|
| 5,336,252 A | 8/1994 | Cohen | |
| 5,458,112 A | 10/1995 | Weaver | |
| 5,478,309 A | 12/1995 | Sweezer et al. | |
| 5,584,803 A | 12/1996 | Stevens et al. | |
| 5,634,895 A | 6/1997 | Igo et al. | |
| 5,792,153 A | 8/1998 | Swain et al. | |
| 5,827,216 A | 10/1998 | Igo et al. | |
| 6,004,269 A | 12/1999 | Crowley et al. | |
| 6,083,166 A | 7/2000 | Holdaway et al. | |
| 6,162,195 A | 12/2000 | Igo et al. | |
| 6,210,323 B1 | 4/2001 | Gilhuly et al. | |
| 6,216,704 B1 | 4/2001 | Ingle et al. | |
| 6,231,518 B1* | 5/2001 | Grabek | A61B 10/06 600/508 |
| 6,398,795 B1 | 6/2002 | McAlister et al. | |
| 6,463,332 B1 | 10/2002 | Aldrich | |
| 6,575,969 B1 | 6/2003 | Rittman et al. | |
| 6,632,227 B2 | 10/2003 | Adams | |
| 6,695,764 B2 | 2/2004 | Silverman et al. | |
| 6,721,663 B1 | 4/2004 | Roberts et al. | |
| 6,837,848 B2 | 1/2005 | Bonner et al. | |
| 6,908,427 B2 | 6/2005 | Fleener et al. | |
| 7,186,252 B2 | 3/2007 | Nobis et al. | |
| 8,602,973 B2 | 12/2013 | Wendlandt | |
| 8,617,150 B2 | 12/2013 | Tsoref et al. | |
| 8,956,346 B2 | 2/2015 | Tsoref et al. | |
| 9,242,122 B2 | 1/2016 | Tsoref et al. | |
| 9,707,414 B2 | 7/2017 | Kardosh et al. | |
| 9,795,450 B2 | 10/2017 | Tsoref et al. | |
| 2001/0041821 A1 | 11/2001 | Wilk | |
| 2001/0053909 A1 | 12/2001 | Nakada et al. | |
| 2002/0002371 A1 | 1/2002 | Acker et al. | |
| 2003/0074057 A1 | 4/2003 | Rosengart | |
| 2003/0187460 A1 | 10/2003 | Chin et al. | |
| 2004/0087831 A1 | 5/2004 | Michels et al. | |
| 2004/0098030 A1 | 5/2004 | Makower et al. | |
| 2004/0216748 A1 | 11/2004 | Chin | |
| 2006/0079868 A1 | 4/2006 | Makin et al. | |
| 2006/0189840 A1 | 8/2006 | Walsh et al. | |
| 2007/0004984 A1 | 1/2007 | Crum et al. | |
| 2007/0010793 A1 | 1/2007 | Callas et al. | |
| 2007/0129719 A1 | 6/2007 | Kendale et al. | |
| 2007/0265610 A1 | 11/2007 | Thapliyal et al. | |
| 2008/0071289 A1 | 3/2008 | Cooper et al. | |
| 2008/0243162 A1 | 10/2008 | Shibata et al. | |
| 2008/0312664 A1 | 12/2008 | Bardsley et al. | |
| 2009/0048514 A1 | 2/2009 | Azhari | |
| 2009/0209986 A1 | 8/2009 | Stewart et al. | |
| 2010/0057108 A1* | 3/2010 | Spivey | A61B 17/06066 606/144 |
| 2010/0125281 A1 | 5/2010 | Jacobson et al. | |
| 2010/0217151 A1 | 8/2010 | Gostout et al. | |
| 2011/0009853 A1 | 1/2011 | Bertolero et al. | |
| 2011/0028998 A1* | 2/2011 | Adams | A61B 17/0469 606/145 |
| 2011/0251524 A1 | 10/2011 | Azhari | |
| 2011/0270239 A1 | 11/2011 | Werneth | |
| 2011/0282203 A1 | 11/2011 | Tsoref et al. | |
| 2011/0282249 A1 | 11/2011 | Tsoref et al. | |
| 2012/0088964 A1 | 4/2012 | Gambhir et al. | |
| 2012/0116158 A1 | 5/2012 | Hale et al. | |
| 2013/0103028 A1 | 4/2013 | Tsoref et al. | |
| 2013/0338545 A1 | 12/2013 | Azhari et al. | |
| 2014/0012083 A1 | 1/2014 | Chin | |
| 2015/0119713 A1 | 4/2015 | Tsoref et al. | |
| 2015/0133946 A1* | 5/2015 | Horvath | A61M 27/002 606/108 |
| 2015/0165244 A1 | 6/2015 | Kardosh et al. | |
| 2015/0182275 A1 | 7/2015 | Tsoref et al. | |
| 2015/0313633 A1 | 11/2015 | Gross et al. | |
| 2015/0313634 A1 | 11/2015 | Gross et al. | |
| 2015/0359558 A1 | 12/2015 | Kardosh et al. | |
| 2016/0107003 A1 | 4/2016 | Tsoref et al. | |

FOREIGN PATENT DOCUMENTS

| | | |
|---|---|---|
| DE | 102006058447 | 6/2008 |
| EP | 1518498 | 3/2005 |
| JP | H11-123197 | 5/1999 |
| JP | 2011-177597 | 9/2011 |
| WO | 1996/000038 | 1/1996 |
| WO | 1996/040368 | 12/1996 |
| WO | 1999/23812 | 5/1999 |
| WO | 1999/59663 | 11/1999 |
| WO | 2007/127664 | 11/2007 |
| WO | 2011/130456 | 10/2011 |
| WO | 2011/141918 | 11/2011 |
| WO | 2013/121424 | 8/2013 |
| WO | 2014/015259 | 1/2014 |
| WO | 2015/170256 | 11/2015 |

OTHER PUBLICATIONS

An Office Action dated Jul. 23, 2018, which issued during the prosecution of U.S. Appl. No. 14/704,857.
An Invitation to pay additional fees dated Jul. 28, 2015, which issued during the prosecution of Applicant's PCT/IB2015/053280.
European Search Opinion dated Oct. 8, 2015, which issued during the prosecution of Applicant's European App No. 13749108.
A Written Opinion dated Nov. 9, 2015, which issued during the prosecution of Applicant's PCT/IB2015/053280.
An International Search Report and a Written Opinion both dated Sep. 18, 2015, which issued during the prosecution of Applicant's PCT/IB2015/055132.
Mi-eye product brochure. Trice Medical. 5pgs. Total.
U.S. Appl. No. 62/250,787, filed Nov. 4, 2015.
U.S. Appl. No. 62/021,327, filed Jul. 7, 2014.
U.S. Appl. No. 61/988,457, filed May 5, 2014.
An Office Action dated May 8, 2014, which issued during the prosecution of U.S. Appl. No. 13/015,951.
An Office Action dated Sep. 22, 2017, which issued during the prosecution of U.S. Appl. No. 14/704,857.
An Office Action dated Jul. 27, 2017, which issued during the prosecution of U.S. Appl. No. 14/324,457.
An International Search Report dated Nov. 9, 2015, which issued during the prosecution of Applicant's PCT/IB2015/053280.
An Office Action dated Feb. 24, 2017, which issued during the prosecution of U.S. Appl. No. 14/324,457.
An International Preliminary Report on Patentability dated Nov. 8, 2016, which issued during the prosecution of Applicant's PCT/IB2015/053280.
An Office Action dated Mar. 15, 2018, which issued during the prosecution of U.S. Appl. No. 14/704,857.
Communication dated Nov. 28, 2018, from United States Patent and Trademark Office in U.S. Appl. No. 15/338,853.
An Office Action together with the English translation dated Sep. 19, 2018, which issued during the prosecution of Chinese Patent Application No. 201580036627.5.

* cited by examiner

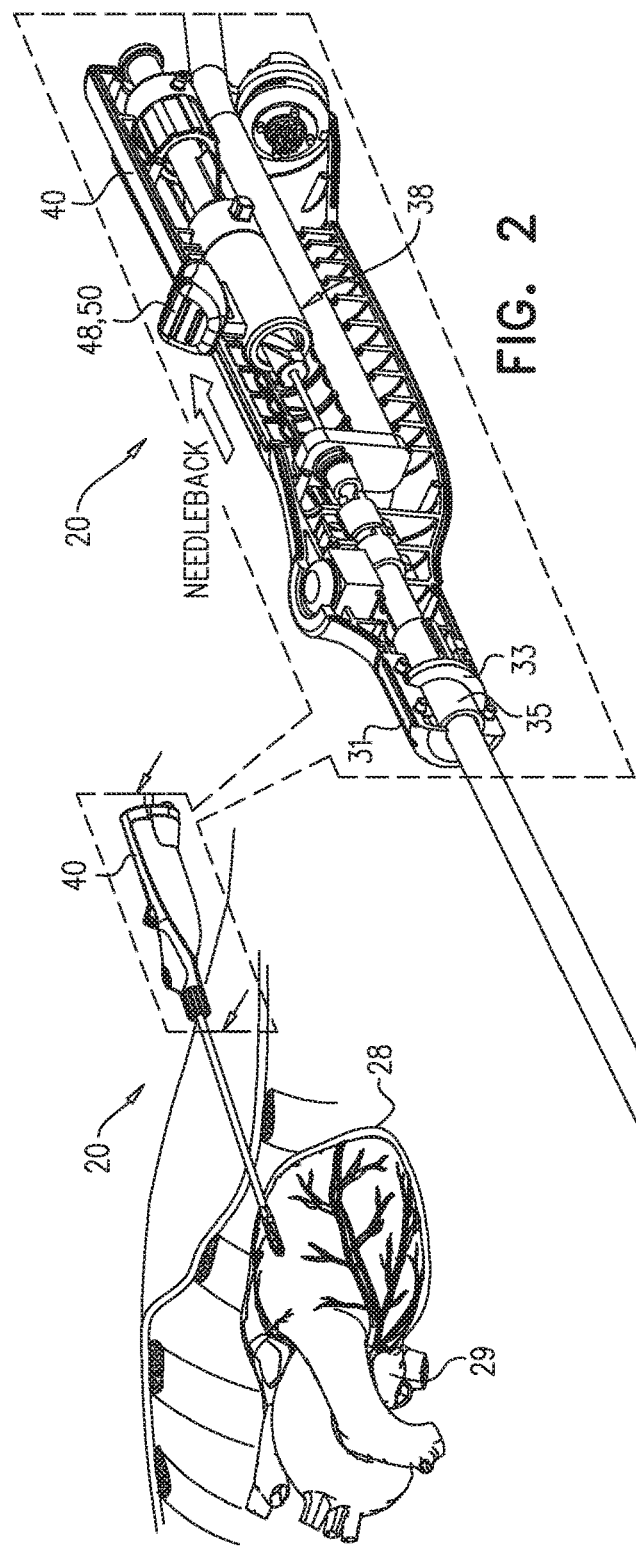
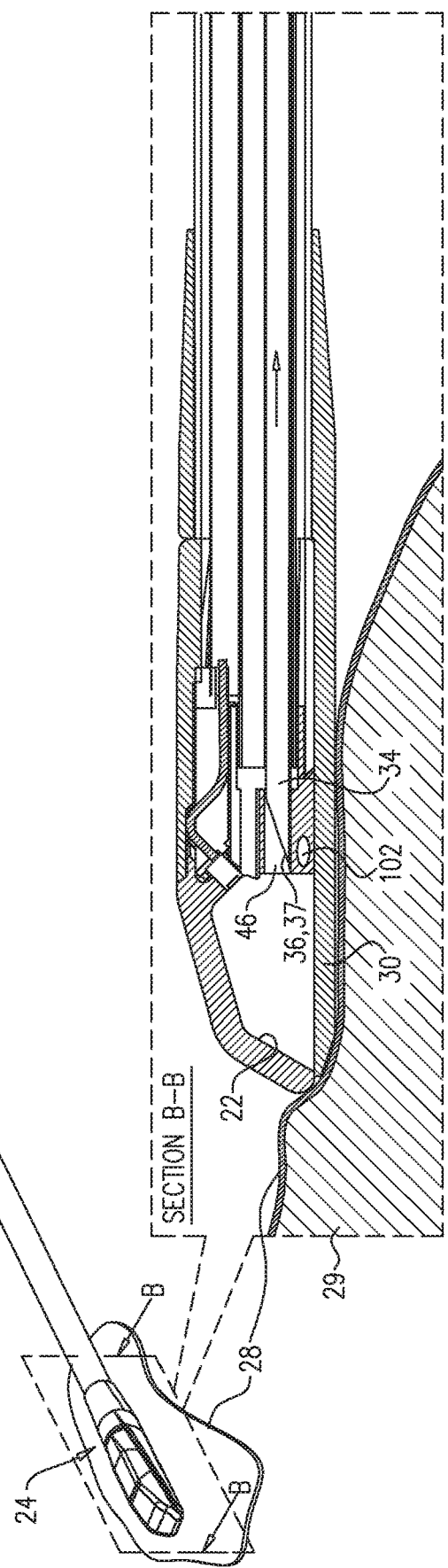
FIG. 2

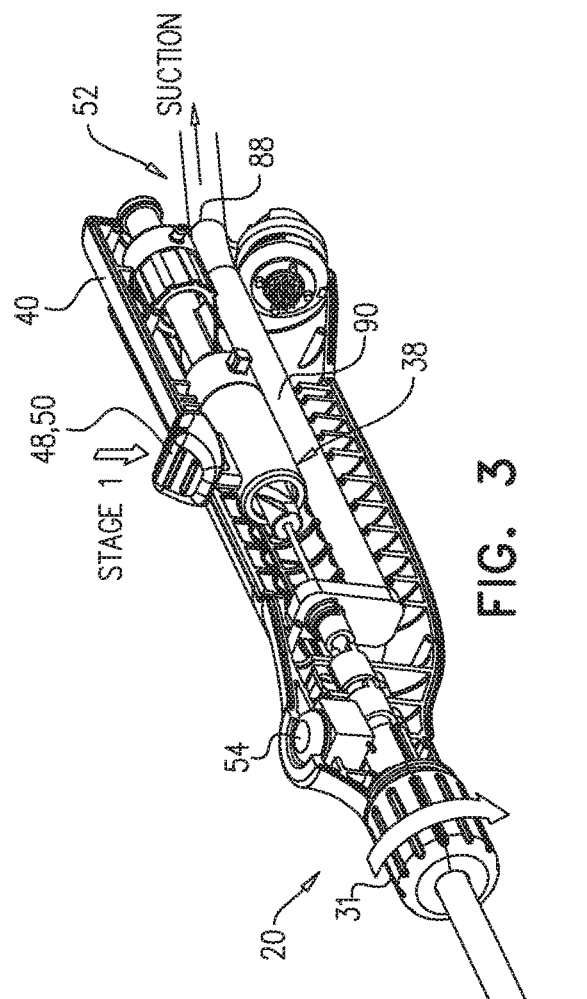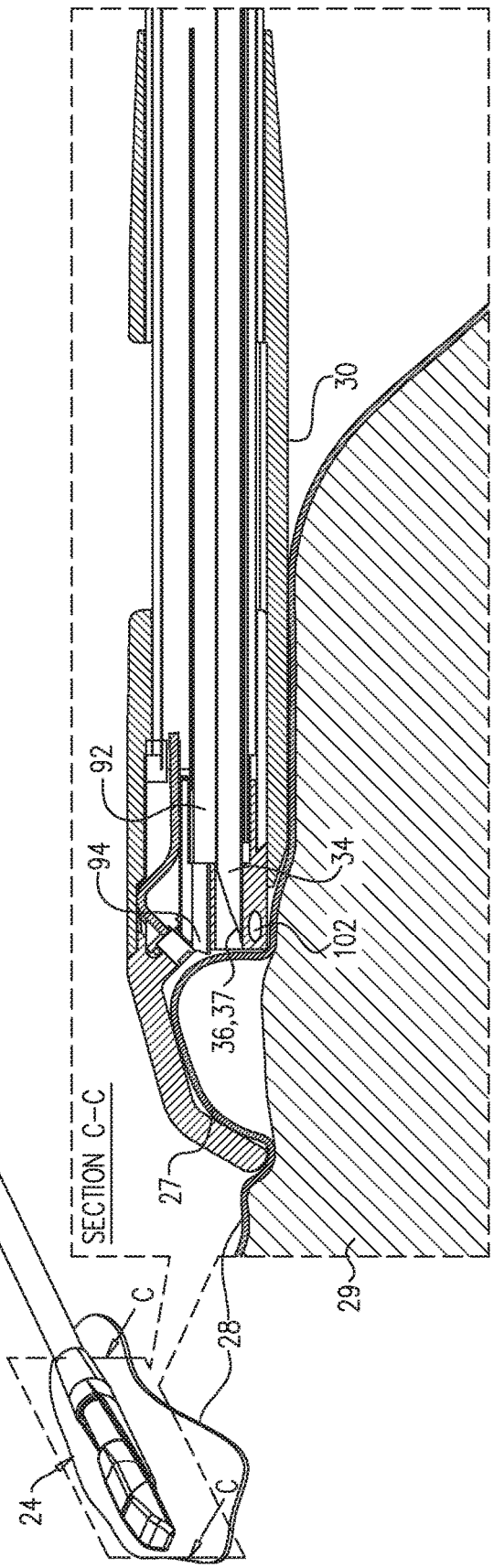
FIG. 3
SECTION C-C

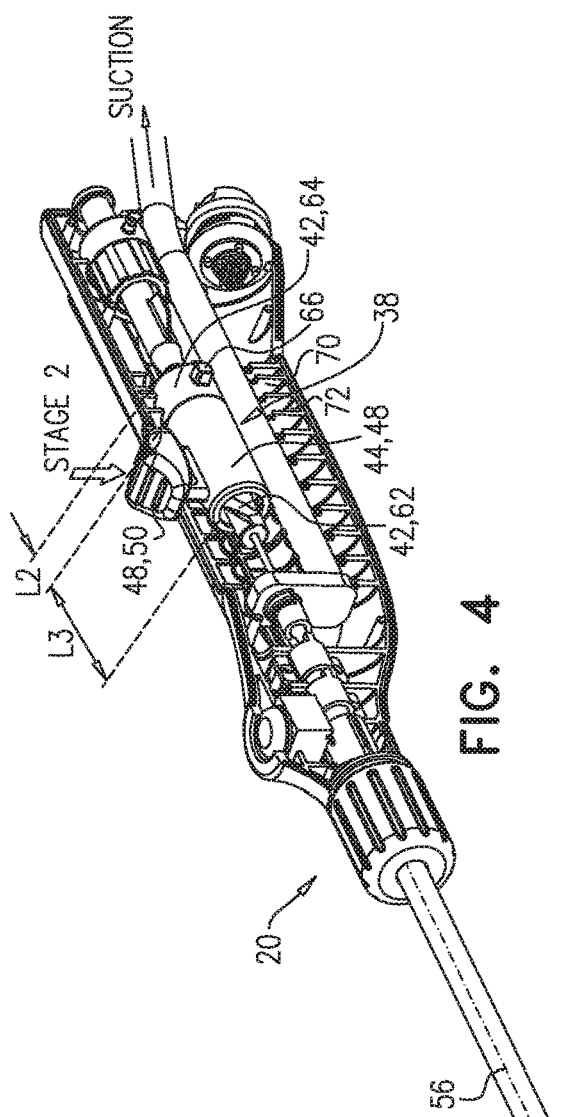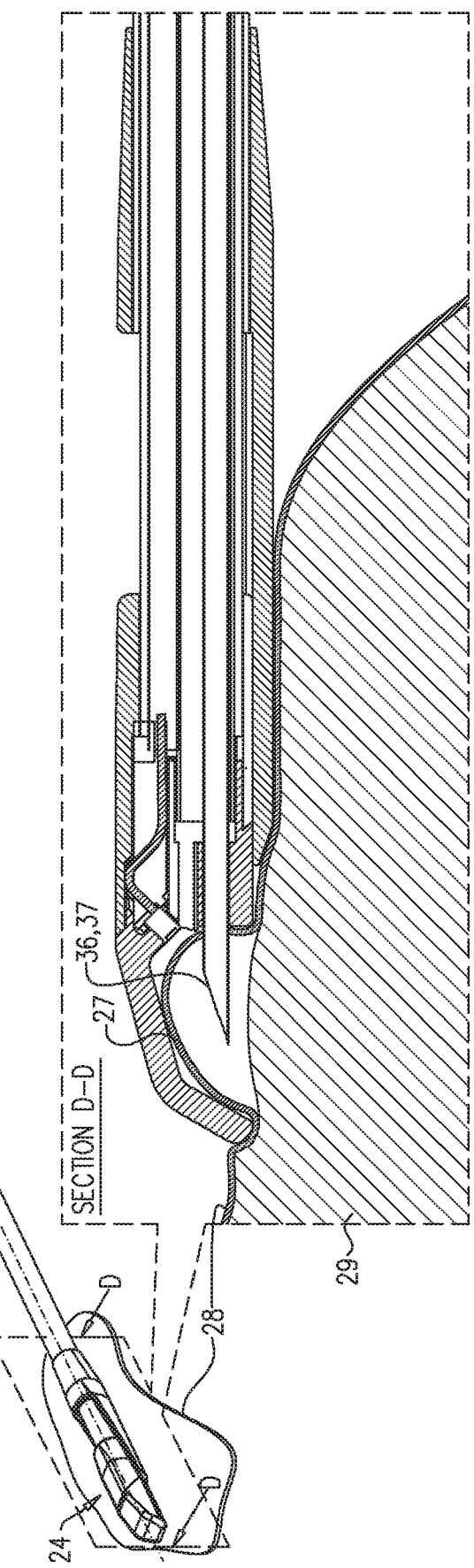
FIG. 4
SECTION D-D

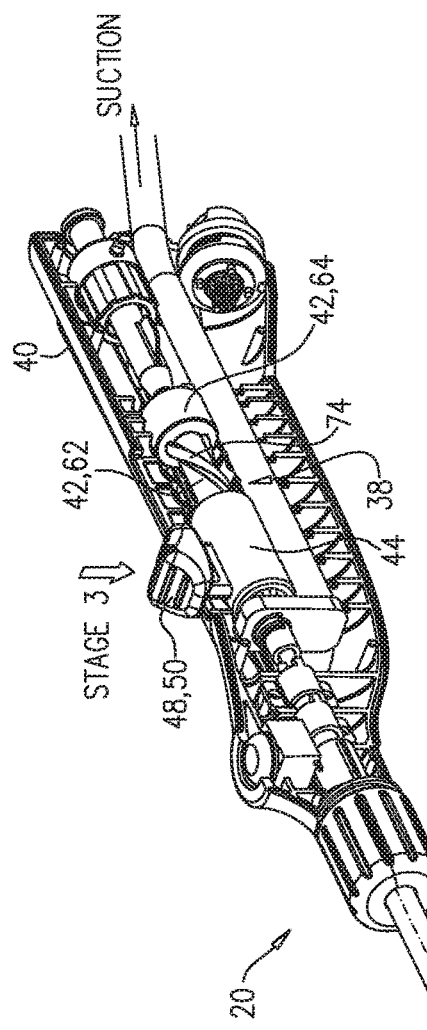
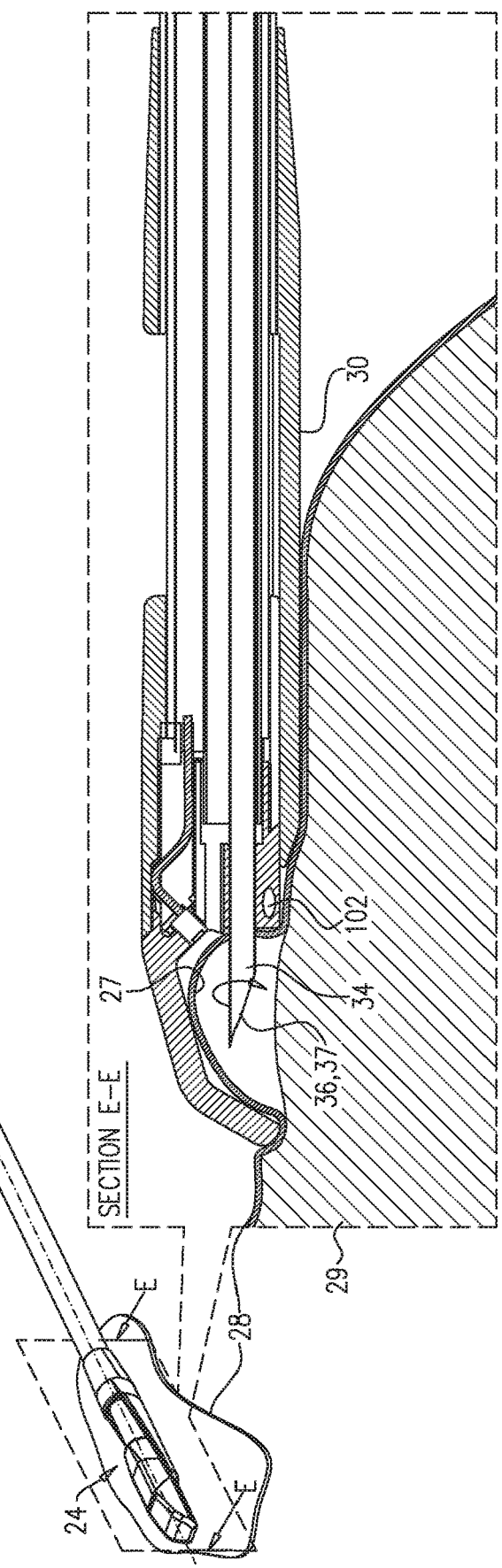
FIG. 5

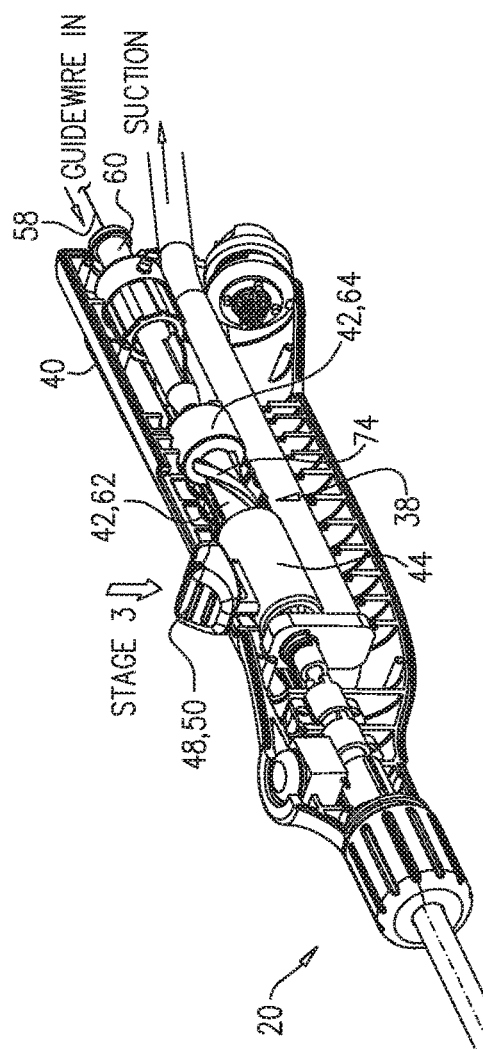
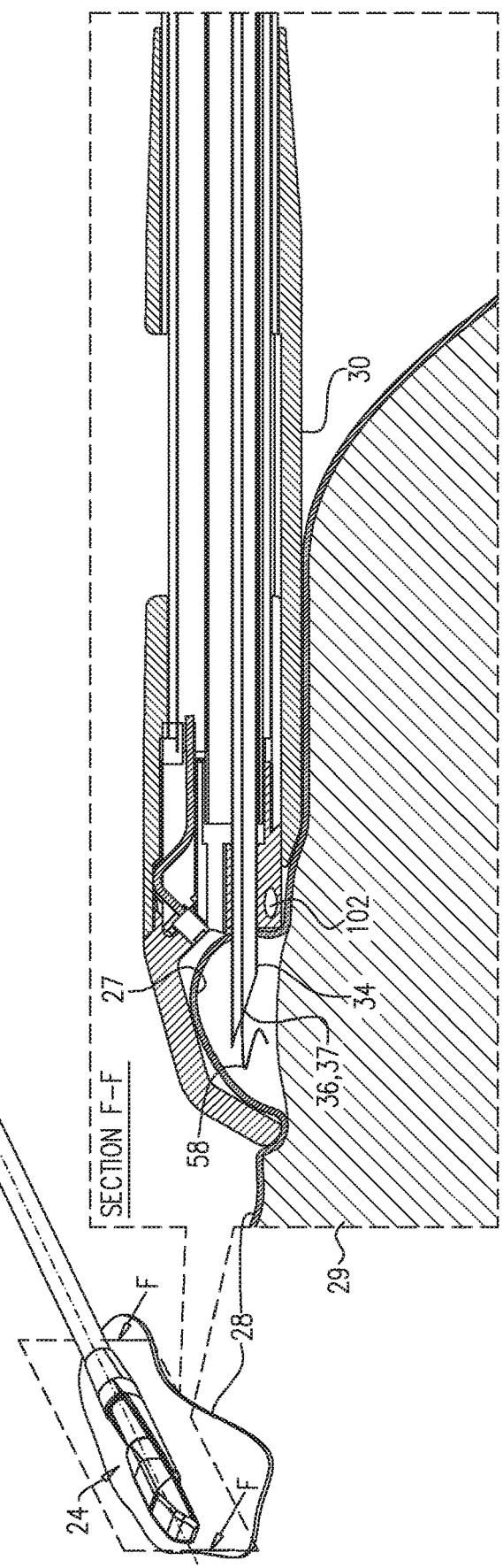
FIG. 6

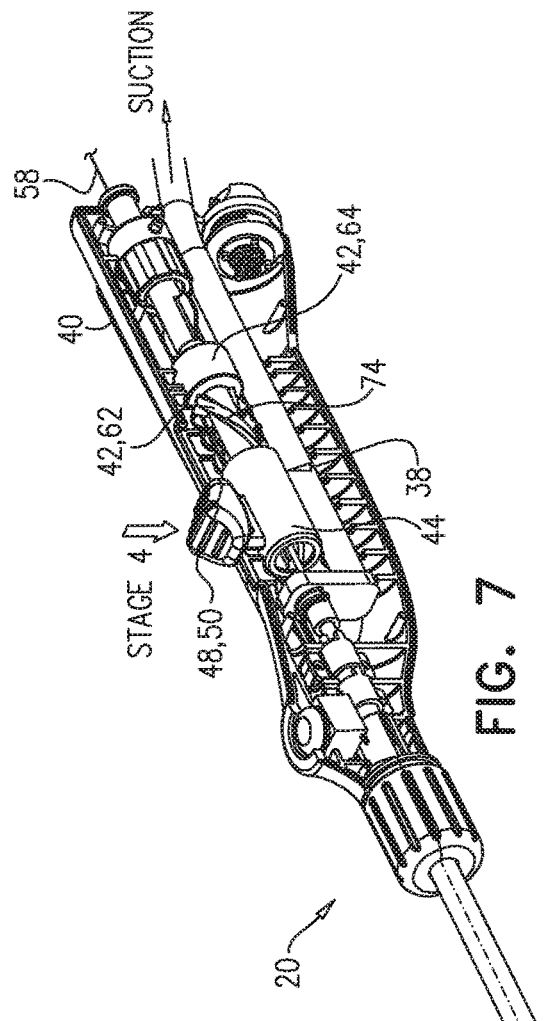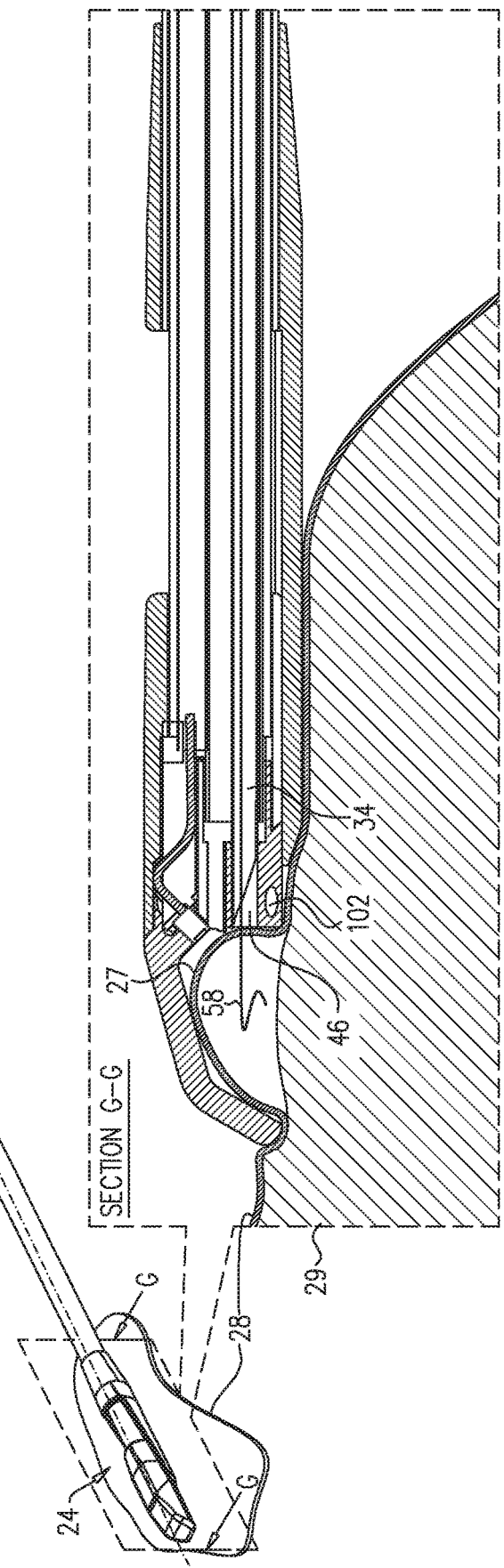

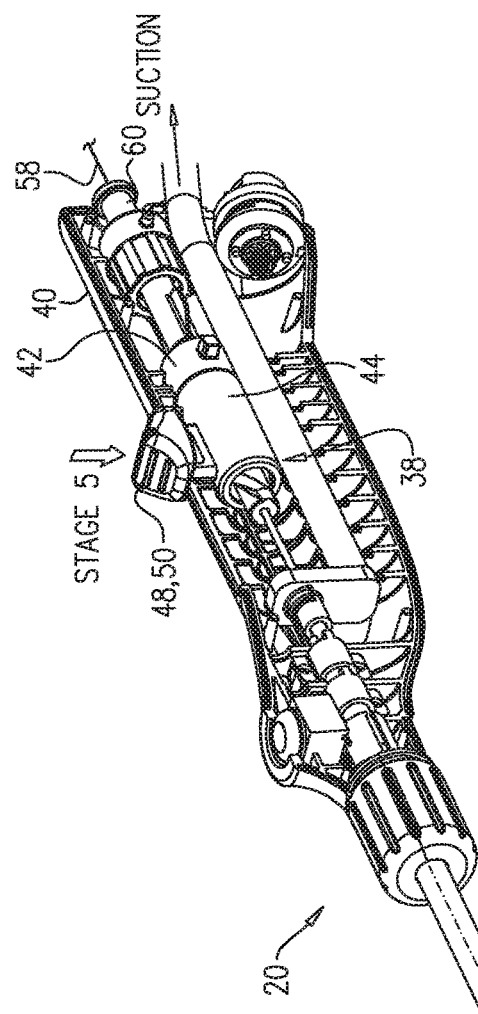
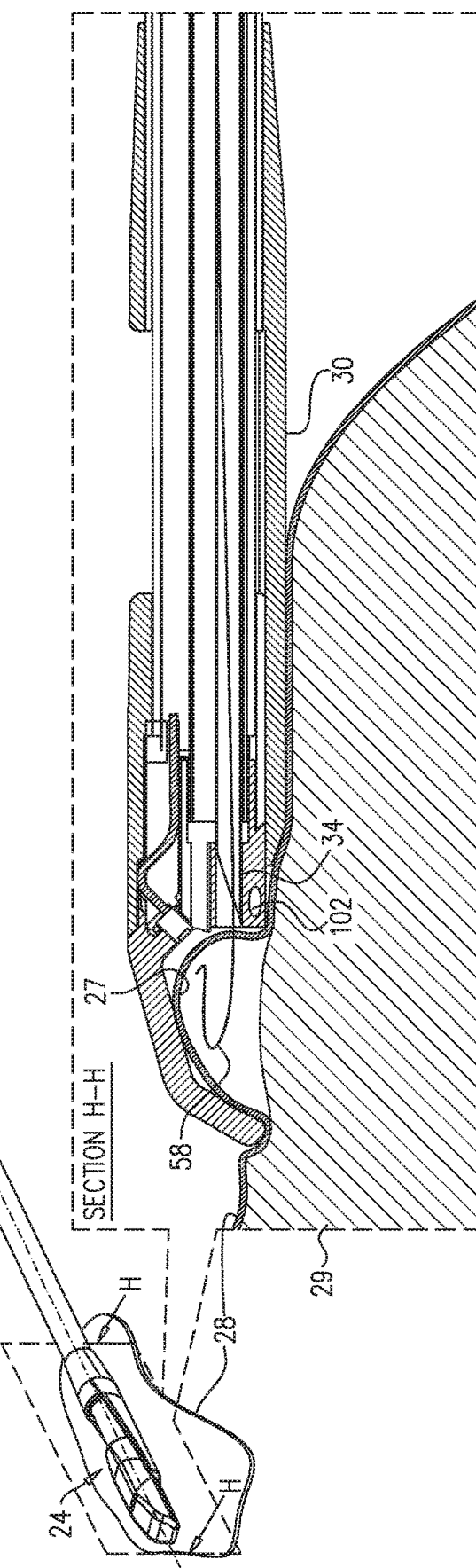
FIG. 8

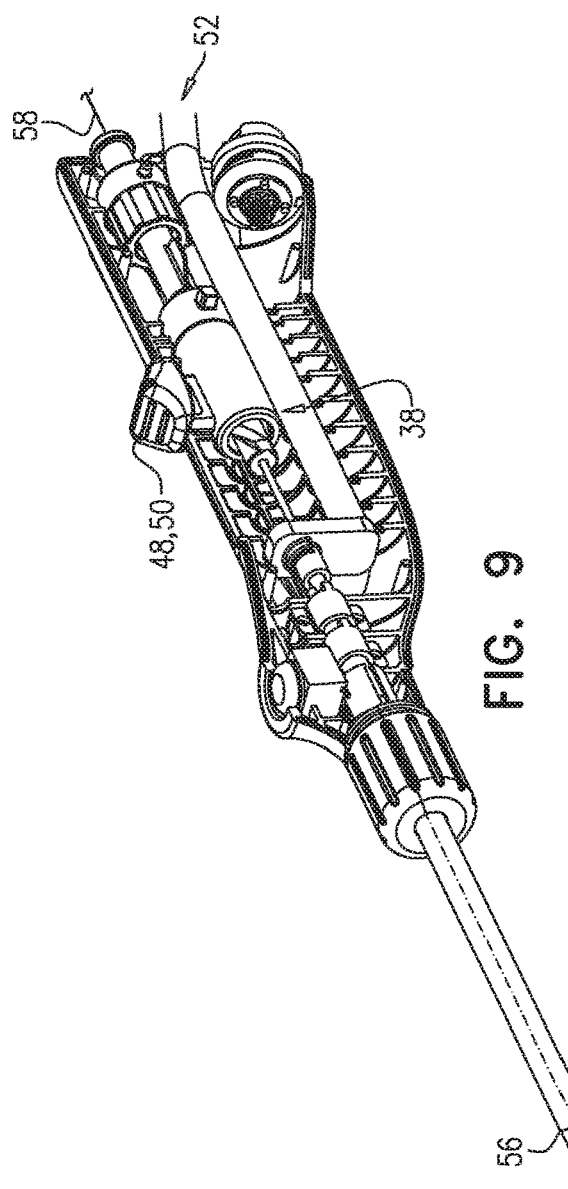
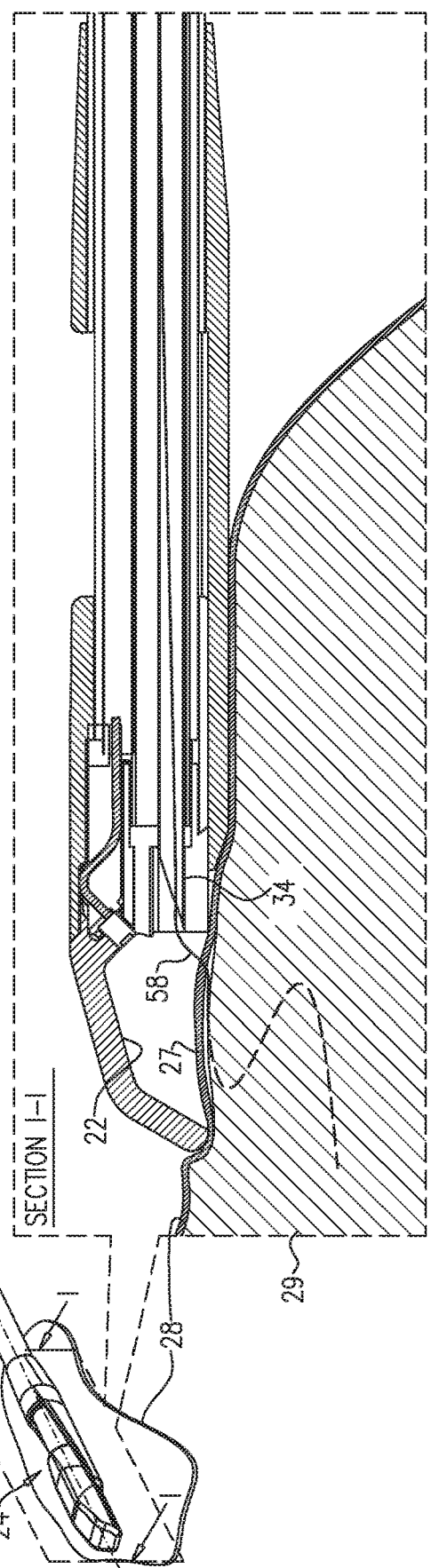
FIG. 9

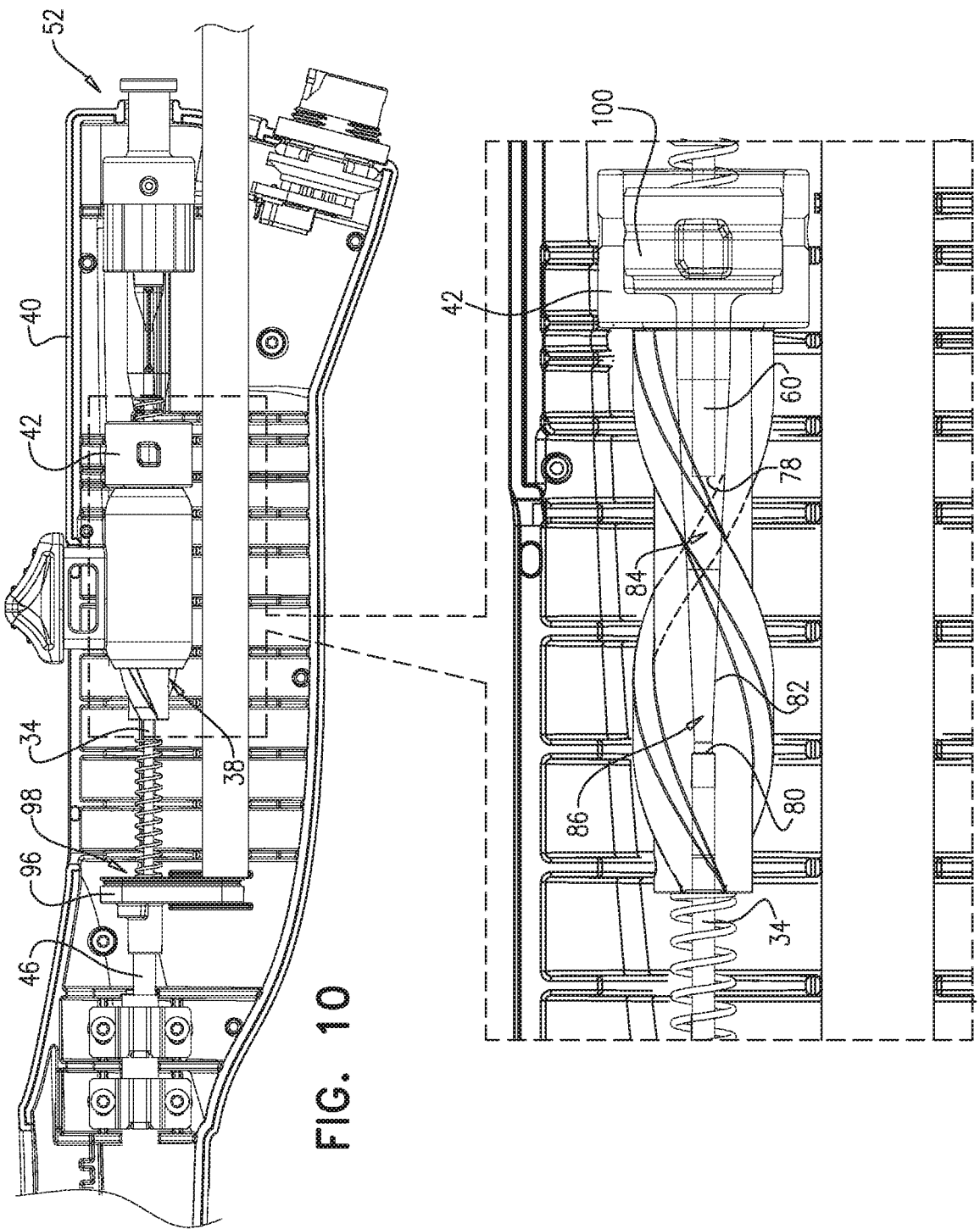

PERICARDIAL NEEDLE MECHANISM

FIELD OF THE INVENTION

Applications of the present invention relate generally to cardiac procedures and specifically to apparatus and methods for accessing a pericardial region, e.g., a pericardial cavity of a subject.

BACKGROUND

The heart is enclosed in a double layered membrane termed the pericardium. The pericardium and its serous fluid protect the heart and lubricate the moving surfaces of the heart. The pericardium is composed of two layers: the outermost fibrous pericardium and the inner serous pericardium. The serous pericardium is divided into two layers, the parietal pericardium, which is fused to the fibrous pericardium, and the visceral pericardium (also termed epicardium). Pericardial serous fluid is found in the pericardial cavity (also termed the pericardial space) between the parietal pericardium and visceral layer.

Accessing of the pericardium may facilitate, for example, drug delivery, a pericardiocentesis procedure (aspiration of pericardial fluid typically for diagnosis of a pericardial disease), left atrial appendage removal, coronary artery bypass grafting, or placement of a reflection-facilitation element as described in US Patent Application Publication 2013/0103028 to Tsoref et al., which issued as U.S. Pat. No. 9,242,122 and which is incorporated herein by reference.

Complications may arise during surgical procedures to access the pericardium, and injury may be caused to internal organs such as the liver, stomach and lungs. Therefore, safe and efficient means of accessing the pericardium are desirable.

SUMMARY OF THE INVENTION

In accordance with some applications of the present invention, a surgical tool is provided for safely accessing a pericardium of a subject and penetrating the pericardium to access a pericardial region. "Pericardial region," as used in the present application, including the claims, consists of one or more regions selected from the group consisting of: a region between the pericardium and the myocardium, a region between the fibrous pericardium and the serous pericardium, a region of the pericardial cavity that is between the parietal pericardium and the visceral pericardium (also known as the epicardium).

Accessing of the pericardial region using any of the techniques described herein is useful during procedures such as a pericardiocentesis procedure in which pericardial fluid is aspirated for the purpose of diagnosing a pericardial disease, or for treatment of cardiac tamponade.

Accessing of the pericardial region using any of the techniques described herein may additionally be useful to apply pressure to bleeding myocardial tissue, typically by accessing the pericardial region and applying pressure to the site of bleeding (e.g., by placing a balloon in the pericardial region using the techniques described herein, and inflating the balloon).

In accordance with some applications of the present invention, the surgical tool is configured to be advanced distally within a body of a subject and shaped such as to allow a physician (e.g., an electrophysiologist) to reach the pericardium while avoiding damage to internal organs, including but not limited to, the liver, the diaphragm, the stomach and the lungs. The surgical tool is shaped to define a side-facing suction port at a distal portion thereof and comprises a slidable transparent shutter which is disposed over the suction and configured to be slidably removed from the suction port. Once the apparatus is in the vicinity of the pericardium, the apparatus contacts an outer surface of the pericardium and applies suction to the tissue in order to draw a portion of the tissue (e.g., a portion of the pericardium) into the surgical tool. Once the tissue is drawn into the surgical tool, the tissue is punctured by a needle that is slidably disposed within the surgical tool.

In accordance with some applications of the present invention, a driving assembly is activated by a user control to drive the needle through a plurality of different movement phases. A distal-mode first phase distally advances the needle into the suction port to puncture the tissue inside the surgical tool, and a distal-mode second phase then rotates the needle about a longitudinal axis of the surgical tool in order to facilitate insertion of a guidewire through the needle and into the pericardial region. Activation of the user control actuates the needle movement phases in succession without requiring a physician to substantially think about and/or activate each phase of the needle movement individually.

For some applications, the surgical tool is shaped to define a lumen and comprises a handle at a proximal end of the surgical tool. The driving assembly is disposed within the handle and has proximal and distal portions that are slidably coupled to each other. The needle is slidably disposed within the lumen and coupled to the proximal portion of the driving assembly, such that (i) during distal advancement of the driving assembly with respect to the handle the needle is advanced distally within the lumen of the surgical tool, the needle being rotationally stationary with respect to a longitudinal axis of the surgical tool, and (ii) subsequently to the needle being advanced distally within the lumen of the surgical tool, distal advancement of the distal portion of the driving assembly with respect to the proximal portion of the driving assembly rotates the needle in a first rotational direction around the longitudinal axis of the surgical tool.

For some applications, a guidewire leading tube is disposed at the proximal end of the handle. At least a distal end of the guidewire leading tube is inside the proximal portion of the driving assembly such that a guidewire can be inserted through the guidewire leading tube and into a proximal end of the needle. Additionally, two gaskets are disposed in the handle to provide a seal around the needle so that a vacuum in the surgical tool is maintained as the needle slides in and out of the suction port. A distal gasket surrounds the needle at a proximal opening of the lumen, and a proximal gasket is disposed between the proximal portion of the driving assembly and the guidewire leading tube.

There is therefore provided, in accordance with some applications of the present invention, apparatus including:

a surgical tool configured to be advanced distally within a body of a subject, the surgical tool: (a) being shaped to define a side-facing suction port at a distal portion of the surgical tool to facilitate drawing tissue through the suction port and into the surgical tool, and (b) including a slidable transparent shutter configured (i) to be disposed over the suction port, and (ii) to be slidably removed from the suction port; and a needle configured to be slidably disposed within the surgical tool and configured to puncture the tissue while the tissue is in the surgical tool.

For some applications, (a) the surgical tool is configured to be advanced distally toward a heart of the subject, (b) the apparatus is configured to facilitate drawing a portion of a pericardium of the heart through the suction port and into the surgical tool, and (c) the slidable transparent shutter is configured (i) to be disposed over the suction port when the surgical tool is advanced distally toward the heart, and (ii) to be slidably removed from the suction port at least when the surgical tool reaches the pericardium of the heart, and the needle is configured to puncture the portion of the pericardium while the portion of the pericardium is in the surgical tool.

For some applications, the side-facing suction port has a width of 2.5-4.5 mm.

For some applications, the side-facing suction port has a length of 8-12 mm.

For some applications, the side-facing suction port has a depth of 3.5-6.5 mm.

For some applications, the side-facing suction port has a width of 2.5-4.5 mm, a length of 8-12 mm, and a depth of 3.5-6.5 mm.

For some applications, the distal portion of the surgical tool has an outer diameter of 8-12 mm.

For some applications, the needle is configured to extend 3-7 mm into the side-facing suction port.

For some applications, the apparatus further includes a sensor configured to (a) detect when the slidable transparent shutter is disposed over the suction port and (b) inhibit application of suction to the suction port when the slidable transparent shutter is disposed over the suction port.

There is further provided, in accordance with some applications of the present invention, a method including:

distally advancing a surgical tool within a body of a subject, the surgical tool (a) shaped to define a side-facing suction port at a distal portion of the surgical tool, and (b) including a slidable transparent shutter disposed over the suction port;

exposing the suction port by sliding the slidable transparent shutter;

subsequently, drawing tissue into the surgical tool by applying suction to the tissue through the suction port; and puncturing the tissue that is in the surgical tool by longitudinally advancing a needle within the surgical tool.

For some applications:

distally advancing includes distally advancing the surgical tool toward a heart of the subject, drawing a portion of tissue into the surgical tool includes drawing a portion of pericardium into the surgical tool by applying suction to the pericardium, and puncturing the tissue includes puncturing the portion of the pericardium by longitudinally advancing a needle within the surgical tool.

For some applications, the method further includes contacting the pericardium with the slidable transparent shutter before the exposing of the suction port.

For some applications, sliding the slidable shutter includes sliding the slidable shutter in a proximal direction to expose the suction port.

There is further provided, in accordance with some applications of the present invention, a method for puncturing a pericardium of a heart of a subject, the method including:

distally advancing a surgical tool toward a heart of a subject, the surgical tool (a) shaped to define a distal end having an outer surface at least part of which is transparent, and (b) shaped to define a suction port at a distal portion of the surgical tool;

drawing a portion of the pericardium into the surgical tool by applying suction to the pericardium through the suction port; and activating a user control to distally advance a driving assembly of the surgical tool, the distal advancement of the driving assembly having a distal-mode first phase and a distal-mode second phase, the distal-mode first phase distally advancing a needle into the suction port while the needle is rotationally stationary with respect to a longitudinal axis of the surgical tool, thereby puncturing the portion of the pericardium within the suction port, and the distal-mode second phase rotating the needle in a first rotational direction while a puncturing tip of the needle is between the pericardium and myocardium of the heart.

For some applications, activating the user control includes executing the distal-mode first and second phases of the distal advancement of the driving assembly in a single smooth motion of the user control.

For some applications, activating the user control includes executing the distal-mode second phase of the distal advancement of the driving assembly to rotate the needle in the first rotational direction without further distally advancing the needle.

For some applications, activating the user control includes executing the distal-mode second phase of the distal advancement of the driving assembly to rotate the needle by 120-240 degrees.

For some applications, activating the user control includes sliding a slide-bar coupled to the driving assembly of the surgical tool.

For some applications, activating the user control includes executing the distal-mode first and second phases or the distal advancement of the driving assembly in a single smooth distally-directed motion of the slide-bar.

For some applications, the method further includes, subsequently to the activating of the user control to distally advance the driving assembly, activating the user control to proximally retract the driving assembly, the proximal retraction having a proximal-mode first phase and a proximal-mode second phase, the proximal-mode first phase retracting the needle proximally into the surgical tool while the needle is rotationally stationary with respect to the longitudinal axis of the surgical tool, and the proximal-mode second phase rotating the needle in a second rotational direction opposite to the first rotational direction For some applications, activating the user control includes executing the proximal-mode first and second phases of the proximally-directed motion in a single smooth motion of the user control.

For some applications, activating the user control includes sliding a slide-bar coupled to the driving assembly of the surgical tool.

For some applications, activating the user control includes executing the proximal-mode first and second phases of the proximal retraction of the driving assembly in a single smooth proximally-directed motion of the slide-bar.

There is further provided, in accordance with some applications of the present invention, apparatus including:

a surgical tool shaped to define a lumen and including a handle disposed at a proximal end of the surgical tool;

a driving assembly disposed within the handle and including proximal and distal portions, the proximal and distal portions being slidably coupled to each other; and a needle slidably disposed within the lumen of the surgical tool and coupled to the proximal portion of the driving assembly such that (i) during distal advancement of the driving assembly with respect to the handle the needle is advanced distally within the lumen of the surgical tool, the needle being rotationally stationary with respect to a longitudinal axis of the surgical tool, and (ii) subsequently to the needle being advanced distally within the lumen of the surgical tool, distal advancement of the distal portion of the driving assembly with respect to the proximal portion of the driving assembly rotates the needle in a first rotational direction around the longitudinal axis of the surgical tool.

For some applications, (i) during proximal retraction of the driving assembly with respect to the handle the needle is retracted proximally within the lumen of the surgical tool, the needle being rotationally stationary with respect to the longitudinal axis of the surgical tool, and (ii) subsequently to the needle being retracted proximally within the lumen of the surgical tool, proximal retraction of the distal portion of the driving assembly with respect to the proximal portion of the driving assembly rotates the needle in a second rotational direction that is opposite to the first rotational direction.

For some applications:

the proximal portion of the driving assembly is shaped to define a thread along at least a portion of the proximal portion, the distal portion of the driving assembly is shaped to define a protrusion, and the proximal and distal portions of the driving assembly are arranged such that (a) the protrusion and the thread engage wait one another and (b) engagement between the protrusion and the thread as the distal portion of the driving assembly is advanced distally with respect to the proximal portion of the driving assembly rotates the needle in the first rotational direction around the longitudinal axis of the surgical tool.

For some applications:

the proximal portion of the driving assembly is shaped to define a protrusion, the distal portion of the driving assembly is shaped to define a thread along at least a portion of the distal portion, and the proximal and distal portions of the driving assembly are arranged such that (a) the protrusion and the thread engage with one another and (b) engagement between the protrusion and the thread as the distal portion of the driving assembly is advanced distally with respect to the proximal portion of the driving assembly rotates the needle in the first rotational direction around the longitudinal axis of the surgical tool.

For some applications:

the proximal portion of the driving assembly is shaped to define a first thread along at least a portion of the proximal portion, the distal portion of the driving assembly is shaped to define a second thread along at least a portion of the distal portion, and the proximal and distal portions of the driving assembly are arranged such that (a) the first and second threads engage one another, and (b) engagement between the first and second threads as the distal portion of the driving assembly is advanced distally with respect to the proximal portion of the driving assembly rotates the needle in the first rotational direction around the longitudinal axis of the surgical tool.

For some applications, engagement between the first and second threads as the distal portion of the driving assembly is retracted proximally with respect to the proximal portion of the driving assembly rotates the needle in the second rotational direction.

For some applications:

the proximal portion of the driving assembly is shaped to define (a) an inner core, the first thread being around a distal length of the inner core, and (b) an outer surface surrounding a proximal length of the inner core, the outer surface being shaped to define a protrusion extending laterally with respect to the longitudinal axis of the surgical tool, and the distal portion of the driving assembly includes a hollow shaft element slidably coupled to the proximal portion of the driving assembly such that prior to distal advancement of the distal portion with respect to the proximal portion, the distal length of the inner core is disposed along the hollow shaft element.

For some applications, prior to distal advancement of the distal portion with respect to the proximal portion, the distal length of the inner core is disposed within the hollow shaft element, the second thread being on an inside surface of the hollow shaft element.

For some applications:

the handle is shaped to define at least one protruding stop on an inner wall of the handle, and the apparatus further includes a user control coupled to the driving assembly and arranged such that a first activation of the user control (a) advances the driving assembly distally within the surgical tool such that (i) the needle is advanced distally within the lumen and (ii) the protrusion engages the at least one protruding stop to lock the proximal portion in place, and (b) subsequently advances the distal portion of the driving assembly distally with respect to the proximal portion of the driving assembly, wherein engagement between the first and second threads as the distal portion is advanced distally with respect to the proximal portion causes rotation of the proximal portion around the longitudinal axis of the surgical tool in the first directional rotation, thereby causing rotation of the needle in the first rotational direction.

For some applications, the user control is arranged such that a second activation of the user control (a) retracts the driving assembly proximally such that the needle is retracted proximally within the lumen and (b) subsequently retracts the distal portion of the driving assembly proximally with respect to the proximal portion of the driving assembly, wherein engagement of the first and second threads as the distal portion is retracted proximally with respect to the proximal direction causes rotation of the proximal portion around the longitudinal axis of the surgical tool in the second rotational direction, thereby causing rotation of the needle in the second rotational direction.

For some applications, the user control includes a slide-bar coupled to the driving assembly and configured to be advanced by a user distally with respect to the handle to cause the first activation and to be retracted by the user proximally with respect to the handle to cause the second activation.

There is further provided, in accordance with some applications of the present invention, apparatus including:

a surgical tool shaped to define a lumen and including a handle disposed at a proximal end of the surgical tool;

a driving assembly disposed within the handle and including proximal and distal portions, the proximal and distal portions being slidably coupled to each other;

a needle slidably disposable within the lumen of the surgical tool, a proximal end of the needle coupled to the proximal portion of the driving assembly such that (i) during distal advancement of the driving assembly with respect to the handle the needle is advanced distally within the lumen of the surgical tool, the needle being rotationally stationary with respect to a longitudinal axis of the surgical tool, and (ii) subsequently to the needle being advanced distally within the lumen of the surgical tool, distal advancement of the distal portion of the driving assembly with respect to the proximal portion of the driving assembly rotates the proximal port of the driving assembly thereby rotating the needle in a first rotational direction around the longitudinal axis of the surgical tool;

a distal gasket surrounding the needle at a proximal opening of the lumen, configured to provide a seal around the needle at the proximal opening of the lumen, the needle being slidable with respect to toe distal gasket;

a guidewire leading tube disposed such that at least a distal end of the guidewire leading tube is inside the proximal portion of the driving assembly; and a proximal gasket disposed between the proximal portion of the driving assembly and the guidewire leading tube, configured to provide a seal between the proximal portion and the guidewire leading tube, the proximal portion and the proximal gasket being configured to move along the outside of the guidewire leading tube during motion of the driving assembly with respect to the handle.

For some applications, the proximal portion of the driving assembly is positioned to guide a guidewire that is passed through the guidewire leading tube into the proximal end of the needle.

For some applications, the proximal portion of the driving assembly is shaped to define an internal funnel, a wider end of the funnel being open to the guidewire leading tube, such that a guidewire that is passed through the guidewire leading tube is guided into the proximal end of the needle by the internal funnel.

For some applications, the proximal portion of the driving assembly is shaped such that a narrow end of the funnel is at the proximal end of the needle.

The present invention will be more fully understood from the following detailed description of applications thereof, taken together with the drawings, in which:

BRIEF DESCRIPTION OF THE DRAWINGS

FIG. 2 is a schematic illustration of the surgical tool showing a cross-section of a handle of the surgical tool, and side-views of the surgical tool within a body of a subject, in accordance with some applications of the present invention;

FIG. 3 is a schematic illustration of the surgical tool showing a portion of tissue drawn into the surgical tool by suction through the surgical tool, in accordance with some applications of the present invention;

FIG. 4 is a schematic illustration of the surgical tool showing a needle puncturing the portion of tissue inside the surgical tool, in accordance with some applications of the present invention;

FIG. 5 is a schematic illustration of the surgical tool showing rotation of the needle after puncturing the portion of tissue, in accordance with some applications of the present invention;

FIG. 6 is a schematic illustration of the surgical tool showing a guidewire being inserted through the rotated needle, in accordance with some applications of the present invention;

FIG. 7 is a schematic illustration of the surgical tool showing the needle being retracted proximally into the surgical tool while in the rotated orientation, in accordance with some applications of the present invention;

FIG. 8 is a schematic illustration of the surgical tool showing rotation of the needle again after the proximal retraction, in accordance with some applications of the present invention;

FIG. 9 is a schematic illustration of the surgical tool after the suction through the surgical tool has been terminated, in accordance with some applications of the present invention; and FIG. 10 is a schematic illustration of a cross-section of a handle of the surgical tool, in accordance with some applications of the present invention.

DETAILED DESCRIPTION

Figure 1:
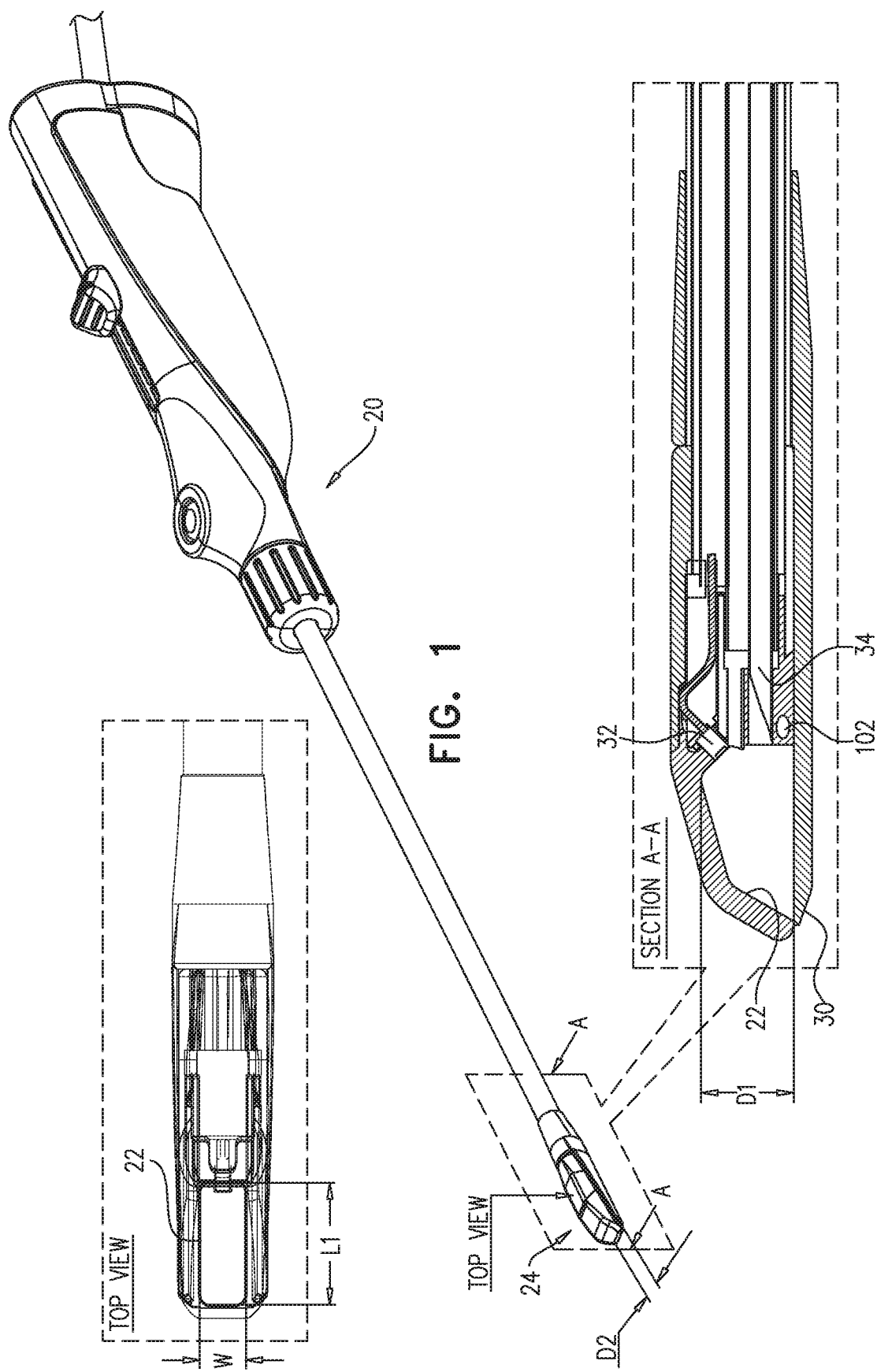
FIG. 1 is a schematic illustration of a surgical tool, including a side-view and top-view of a distal portion of the surgical tool, in accordance with some applications of the present invention.

Reference is now made to FIG. 1, which is a schematic illustration of a surgical tool 20 in accordance with some applications of the present invention. Surgical tool 20 is designed to be advanced distally within a body of a subject, e.g., toward a heart of a subject, and is shaped to define a side-facing suction port 22 at a distal portion 24 of surgical tool 20 to facilitate drawing tissue 26, e.g., a portion 27 of the pericardium 28 of a subject (such as is shown in FIG. 3) into surgical tool 20. Tissue 26 is drawn into surgical tool 20 by applying suction to tissue 26 through side-facing suction port 22. A needle 34 is slidably disposed within surgical tool 20 and is used to puncture tissue 26, e.g., portion 27 of pericardium 28, by advancing needle 34 distally into side-facing suction port 22 while tissue 26 is inside side-facing suction port 22.

For some applications, side-facing suction port 22 has the following dimensions:
- a width W of at least 2.5 mm and/or less than 4.5 mm,
- a length L1 of at least 8 mm and/or less than 12 mm, such that needle 34 can extend at least 3 mm and/or less than 7 mm into side-facing suction port 22, and/or
- a depth D1 of at least 3.5 mm and/or less than 6.5 mm.

For some applications, distal portion 24 of surgical tool 20 has an outer diameter of at least 8 mm and/or less than 12 mm.

Experiments performed by the inventors on human pericardium have shown that these dimensions work particularly well to draw the pericardium into the surgical tool, maintain the pericardium there, and facilitate insertion of a needle through the pericardium.

For some applications, a slidable transparent shutter 30 is disposed over side-facing suction port 22 to help prevent fat and/or tissue from building up inside side-facing suction port 22 as surgical tool 20 is advanced distally within the body. Slidable transparent shutter 30 can be slidably removed from side-facing suction port 22 once tissue 26 is reached, e.g., once pericardium 28 is reached (such as is shown in FIG. 3). For example, slidable transparent shutter 30 may be slidably removed by sliding the shutter in a proximal direction, thus exposing side-facing suction port 22. For some applications use of surgical tool 20 includes contacting pericardium 28 with slidable transparent shutter 30 before exposing side-facing suction port 22 (such as is shown in FIG. 2). For some applications, slidable transparent shutter 30 is removed by turning a rotational actuator 31 on surgical tool 20 (such as is shown in FIG. 3). Rotational actuator 31 engages threads 33 on a pulling screw 35, which pulls slidable transparent shutter 30 in a proximal direction thus exposing side-facing suction port 22.

A camera 32 is positioned in distal portion 24 such that a view from camera 32 is through side-facing suction port 22. Thus, the transparency of slidable transparent shutter 30 helps to maintain visibility. LED lighting (or other lighting)

may also be used inside surgical tool 20 to assist visibility through camera 32. For some applications, surgical tool 20 comprises a sensor 102 configured to (a) detect when slidable transparent shutter 30 is disposed over suction port 22 and (b) inhibit application of suction to side-facing suction port 22 when slidable transparent shutter 30 is disposed over side-facing suction port 22.

Reference is now made to FIG. 2, which is a schematic illustration of surgical tool 20, showing a cross-section of a handle 40 of surgical tool 20, and side-views of surgical tool 20 within a body of a subject, in accordance with some applications of the present invention. Needle 34 is a hollow needle shaped to define a slanted puncturing tip 36. For puncturing portion 27 of pericardium 28, it is advantageous to have needle 34 oriented such that an opening 37 at puncturing tip 36 of needle 34 faces away from the myocardium 29 of the subject (such as is shown in FIG. 4). However, for inserting a guidewire through needle 34 into the pericardial region, it is advantageous to have needle 34 oriented such that opening 37 at puncturing tip 36 faces myocardium 29 (such as is shown in FIG. 6). A user-control-activated driving assembly 38 is used to drive and rotate needle 34 within lumen 46. FIG. 2 shows driving assembly 38 and needle 34 in starting position. As can be seen in cross-section B-B, prior to distal advancement of driving assembly 38, opening 37 at puncturing tip 36 of needle 34 faces away from myocardium 29 and is fully inside lumen 46 of surgical tool 20.

For some applications, a user control 48, is coupled to driving assembly 38 and is used to activate driving assembly 38 to drive needle 34 within lumen 46. A first activation of user control 48 distally advances driving assembly 38 in two distal-mode phases:
  a distal-mode first phase, in which needle 34 is advanced distally within lumen 46 while remaining rotationally stationary with respect to a longitudinal axis 56 of surgical tool 20, thereby puncturing tissue 26 inside side-facing suction port 22, e.g., puncturing portion 27 of pericardium 28 (such as is shown in FIG. 4), and
  a distal-mode second phase, in which needle 34 is rotated in a first rotational direction about longitudinal axis 56 while puncturing tip 36 of needle 34 is between pericardium 28 and myocardium 29 of the heart (such as is shown in FIG. 5).
A second activation of user control 48 proximally retracts driving assembly 38 in two proximal-mode phases:
  a proximal-mode first phase, in which needle 34 is proximally retracted into lumen 46 of surgical tool 20 while remaining rotationally stationary with respect to longitudinal axis 56 of surgical tool 20 (such as is shown in FIG. 7), and
  a proximal-mode second phase, in which needle 34 is rotated in a second rotational direction opposite to the fist rotational direction about longitudinal axis 56 (such as is shown in FIG. 8).

For some applications, each of the first and second activations of user control 48 are executed in single smooth respective motions of user control 48, i.e., the distal-mode first phase and distal mode second phase are executed in a first single smooth motion of user control 48 and then the proximal-mode first phase and proximal-mode second phase are executed in a second single smooth motion of user control 48. For some applications, user control 48 may be a slide-bar 50 that is coupled to driving assembly 38. Slide-bar 50 is configured to be advanced distally with respect to handle 40 in order to cause the first activation, and to be retracted proximally with respect to handle 40 in order to cause the second activation. Thus, the distal-mode first phase and distal-mode second phase are executed in a single smooth distally-directed motion of slide-bar 50 with respect to handle 40, and the proximal-mode first phase and proximal-mode second phase are executed in a single smooth proximally-directed motion of slide-bar 50 with respect to handle 40. Thus, for these applications, the respective single smooth motions of user control 48, e.g., slide-bar 50, do not require that surgical tool 20 provides feedback to a physician, that would allow the physician to terminate the motion of needle 34 before entering the respective second phase. Thus, the physician does not have to substantially think about each phase of the needle movement individually.

Reference is now made to FIG. 3, which is a schematic illustration of surgical tool 20 showing a portion of tissue drawn into surgical tool 20 by suction through surgical tool 20, in accordance with some applications of the present invention. After slidable transparent shutter 30 is removed from side-facing suction port 22, suction is applied to pericardium 28 through a proximal opening 88 of an external vacuum tube 90 which is disposed within handle 40 of surgical tool 20. Proximal opening 88 of external vacuum tube 90 is disposed at a proximal end 52 of handle 40. External vacuum tube 90 sealably connects to an internal vacuum tube 92 which is disposed along-side lumen 46 in surgical tool 20 and has a distal opening 94 inside side-facing suction port 22. Due to the open side-facing suction port 22 being in contact with pericardium 28, a vacuum is created when the suction is applied, thereby pulling portion 27 of pericardium 28 into side-facing suction port 22. A vacuum activation user control 54 is disposed on handle 40.

Reference is now made to FIGS. 4-6, which are schematic illustrations of surgical tool 20 showing the distal-mode phases of motion of needle 34, in accordance with some applications of the present invention. For some applications, driving assembly 38 has a proximal portion 42 and a distal portion 44 that are slidably coupled to each other. Needle 34, which is slidably disposed within a lumen 46 of surgical tool 20, is coupled to proximal portion 42 of driving assembly 38 (such as is shown in FIG. 10).

During the distal-mode first phase, driving assembly 38 is advanced distally with respect to handle 40 (FIG. 4). Thus, needle 34 is advanced distally within lumen 46 of surgical tool 20, thereby puncturing portion 27 of pericardium 28. Needle 34 is rotationally stationary with respect to longitudinal axis 56 of surgical tool 20 during the distal-mode first phase. Subsequently, during the distal-mode second phase, distal portion 44 of driving assembly 38 is advanced distally with respect to proximal portion 42 of driving assembly 38 (FIG. 5). Distal advancement of distal portion 44 of driving assembly 38 with respect to proximal portion 42 of driving assembly 38 rotates needle 34 in a first rotational direction about longitudinal axis 56 of surgical tool 20 while puncturing tip 36 of needle 34 is between pericardium 28 and myocardium 29 of the heart. The distal-mode second phase typically rotates needle 34 by 120-240 degrees without further distal advancement of needle 34.

For some applications, proximal portion 42 of the driving assembly is shaped to define (a) an inner core 62, and (b) an outer surface 64 surrounding a proximal length L2 of inner core 62. Outer surface 64 is shaped to define a protrusion 66 extending laterally with respect to longitudinal axis 56 of surgical tool 20. Distal portion 44 of driving assembly 38 comprises a hollow shaft element 68 which is slidably coupled to proximal portion 42 of driving assembly 38 such that prior to distal advancement of distal portion 44 with respect to proximal portion 42, a distal length L3 of inner core 62 is disposed along hollow shaft element 68, e.g., within hollow shaft element 68. Handle 40 of surgical tool 20 is shaped to define at least one protruding stop 70 on an inner wall 72 of handle 40. The first activation of user control 48 causes driving assembly 38 to be advanced distally with respect to handle 40 until protrusion 66 engages protruding stop 70, which locks proximal portion 42 of driving assembly 38 in place, thus marking the end of the distal-mode first phase. The remainder of the first activation of user control 48, during the distal-mode second phase, subsequently advances distal portion 44 of driving assembly 38 with respect to proximal portion 42 of driving assembly 38. As described hereinbelow, a mechanical interaction between proximal portion 42 and distal portion 44 of driving assembly 38 during the distal-mode second phase causes needle 34 to rotate about longitudinal axis 56.

For some applications, proximal portion 42 of driving assembly 38 is shaped to define a first thread 74 (FIG. 10) along at least a portion of proximal portion 42, e.g., along distal length L3 of inner core 62, and distal portion 44 of driving assembly 38 is shaped to define a second thread 76 along at least a portion of distal portion 44, e.g., on an inside surface of hollow shaft element 68. Proximal portion 42 and distal portion 44 of driving assembly 38 are arranged such that (a) first thread 74 and second thread 76 engage one another (such as is shown in FIG. 10), and (b) engagement between first thread 74 and second thread 76 as distal portion 44 of driving assembly 38 is advanced distally with respect to proximal portion 42 of driving assembly rotates needle 34 in the first rotational direction about longitudinal axis 56.

Alternatively, proximal portion 42 of driving assembly 38 is shaped to define a thread along at least a portion of proximal portion 42, e.g., along distal length L3 of inner core 62, and distal portion 44 of driving assembly 38 is shaped to define a protrusion (configuration not shown). Proximal portion 42 and distal portion 44 of driving assembly 38 are arranged such that (a) the protrusion and the thread engage with one another, and (b) engagement between the protrusion and the thread as distal portion 44 of driving assembly 38 is advanced distally with respect to proximal portion 42 of driving assembly 38 rotates needle 34 in the first rotational direction about longitudinal axis 56.

Alternatively, proximal portion 42 of driving assembly 38 is shaped to define a protrusion, and distal portion 44 of driving assembly 38 is shaped to define a thread along at least a portion of distal portion 44, e.g., on an inside surface of hollow shaft element 68 (configuration not shown). Proximal portion 42 and distal portion 44 of driving assembly 38 are arranged such that (a) the protrusion and the thread engage with one another, and (b) engagement between the protrusion and the thread as distal portion 44 of driving assembly 38 is advanced distally with respect to proximal portion 42 of driving assembly 38 rotates needle 34 in the first rotational direction about longitudinal axis 56.

Once needle 34 has punctured pericardium 28, a guide-wire 58 is inserted through a guide-wire leading tube 60, as further described hereinbelow. The rotated position of needle 34 facilitates easy insertion of guidewire 58 through needle 34 into the pericardial region (FIG. 6). For some applications fluoroscopy is used to help determine that guidewire 58 is in the pericardial region.

Reference is now made to FIGS. 7-8, which are schematic illustrations of surgical tool 20 showing the proximal-mode phases of motion of needle 34, in accordance with some applications of the present invention. The second activation of user control 48, e.g., the proximally-directed motion of slide-bar 50, activates the proximal-mode first and second phases. During the proximal-mode first phase, driving assembly 38 is retracted proximally with respect to handle 40 (FIG. 7), causing needle 34 to be retracted proximally into lumen 46 of surgical tool 20. Needle 34 is rotationally stationary with respect to longitudinal axis 56 during proximal-mode first phase. Subsequently, during the proximal-mode second phase, distal portion 44 of driving assembly 38 is retracted proximally with respect to proximal portion 42 of driving assembly 38 (FIG. 8). Proximal retraction of distal portion 44 with respect to proximal portion 42 of driving assembly 38 rotates needle 34 in the second rotational direction opposite the first rotational direction about longitudinal axis 56. After the proximal-mode second phase, needle 34 is in the same position as it was prior to the distal-mode first phase. Similarly to the first rotation of needle 34, engagement between first thread 74 and second thread 76 as distal portion 44 of driving assembly 38 is retracted proximally with respect to proximal portion 42 of driving assembly 38 rotates needle 34 in the second rotational direction about longitudinal axis 56.

Reference is now made to FIG. 9, which is a schematic illustration of surgical tool 20 after the suction through surgical tool 20 has been terminated, in accordance with some applications of the present invention. Once the suction has been terminated, portion 27 of pericardium 28 resumes its original position with respect to the heart, with guidewire 58 now inside the pericardial region. Surgical instruments can be inserted into the pericardial region along guidewire 58.

Reference is now made to FIG. 10, which is a schematic illustration of a cross-section of handle 40 of surgical tool 20, in accordance with some applications of the present invention. In order to facilitate insertion of guidewire 58 into needle 34, guidewire leading tube 60 is disposed in proximal end 52 of handle 40 such that at least a distal end 78 of guidewire leading tube 60 is inside proximal portion 42 of driving assembly 38. Guidewire 58 is inserted through guidewire leading tube 60 into proximal portion 42 of driving assembly 38. Proximal portion then guides guidewire 58 from guidewire leading tube 60 to a proximal end 80 of needle 34. For example, proximal portion 42 may be shaped to define an internal funnel 82, a wider end 84 of funnel 82 being open to guidewire leading tube 60, such that guidewire 58 is guided into proximal end 80 of needle 34 by funnel 82. For some applications, a narrow end 86 of funnel 82 is at proximal end 80 of needle 34.

Reference is again made to FIG. 3, as well as to FIG. 10. It is desirable that the vacuum which keeps portion 27 of pericardium 28 inside side-facing suction port 22, be maintained throughout the motion of needle 34 into and subsequently back out of side-facing suction port 22, as well as throughout insertion of guidewire 58. For some applications, this is achieved by using two gaskets. A distal gasket 96 surrounds needle 34 at a proximal opening 98 of lumen 46. Distal gasket 96 provides a seal around needle 34 at proximal opening 98 of lumen 46, thus preventing premature termination of the vacuum by preventing air from entering side-facing suction port 22 through lumen 46 as needle 34 slides with respect to lumen 46. Needle 34 is slidable with respect to distal gasket 96 as well. A proximal gasket 100 is disposed between proximal portion 42 of driving assembly 38 and guidewire leading tube 60. Proximal gasket 100 provides a seal between guidewire leading tube 60 and proximal portion 42. Proximal portion 42 of driving assembly 38 and proximal gasket 100 move along the outside of guidewire leading tube 60 during motion of driving assembly with respect to handle 40 of surgical tool 20.

Included in the scope of the present invention are applications of surgical tool 20 to anatomy other than the heart of a subject. For example, surgical tool 20 may be used to puncture an outer layer of a stomach, intestine, or brain of a subject. All features of the present invention as described hereinabove apply to applications of surgical tool 20 with anatomy other than the heart. Similarly to puncturing pericardium 28, surgical tool is advanced within the body of a subject until slidable transparent shutter 30 comes into contact with the target tissue, stomach, intestine, and/or brain. Slidable transparent shutter 30 is then removed from side-facing suction port 22 and suction is applied to draw a portion of the tissue into side-facing suction port 22. Activation of user control 48 drives needle 34 to puncture the tissue and guidewire 58 can be inserted.

Techniques and applications described in the present application may be combined with techniques and applications described in any of the following applications, each of which is incorporated herein by reference:

(a) U.S. application Ser. No. 14/324,457 to Gross et al., which published as US 2015-0313633, entitled "Pericardial Access Device," filed Jul. 7, 2014, (b) U.S. application Ser. No. 14/704,857 to Gross et al., which published as US 2015-0313634, entitled "Pericardial Access Device," filed May 5, 2015, (c) PCT Application No. PCT/IB2015/053280 to Gross et al., which published as WO/2015/170256, entitled "Pericardial Access Device," filed May 5, 2015, (d) U.S. application Ser. No. 15/338,853 to Gross et al., which published as US 2017-0119435 to Gross, entitled "Pericardial Access Device," filed Oct. 31, 2016, and (e) U.S. application Ser. No. 15/324,429 to Gross et al., which published as US 2017/0196568 to Gross, entitled "Left Atrial Appendage Closure," filed Jan. 6, 2017.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for puncturing a pericardium of a heart of a subject, the method comprising:
    using apparatus comprising:
        a surgical tool shaped to define a lumen and comprising a handle disposed at a proximal end of the surgical tool;
        a driving assembly disposed within the handle and comprising proximal and distal portions, the proximal and distal portions being slidably coupled to each other; and
        a needle slidably disposed within the lumen of the surgical tool and coupled to the proximal portion of the driving assembly such that (i) during distal advancement of the driving assembly with respect to the handle the needle is advanced distally within the lumen of the surgical tool, the needle being rotationally stationary with respect to a longitudinal axis of the surgical tool, and (ii) subsequently to the needle being advanced distally within the lumen of the surgical tool, distal advancement of the distal portion of the driving assembly with respect to the proximal portion of the driving assembly rotates the needle in a first rotational direction around the longitudinal axis of the surgical tool;

distally advancing the surgical tool toward the heart of a subject, the surgical tool (a) shaped to define a distal end having an outer surface at least part of which is transparent, and (b) shaped to define a suction port at a distal portion of the surgical tool;

drawing a portion of the pericardium into the surgical tool by applying suction to the pericardium through the suction port; and activating a user control to distally advance the driving assembly of the surgical tool, the distal advancement of the driving assembly having a distal-mode first phase and a distal-mode second phase,
    the distal-mode first phase distally advancing the needle into the suction port while the needle is rotationally stationary with respect to the longitudinal axis of the surgical tool, thereby puncturing the portion of the pericardium within the suction port, and
    the distal-mode second phase rotating the needle in the first rotational direction while a puncturing tip of the needle is between the pericardium and myocardium of the heart.

2. The method according to claim 1, wherein activating the user control comprises executing the distal-mode first and second phases of the distal advancement of the driving assembly in a single smooth motion of the user control.

3. The method according to claim 1, wherein activating the user control comprises executing the distal-mode second phase of the distal advancement of the driving assembly to rotate the needle in the first rotational direction without further distally advancing the needle.

4. The method according to claim 1, wherein activating the user control comprises executing the distal-mode second phase of the distal advancement of the driving assembly to rotate the needle by 120-240 degrees.

5. The method according to claim 1, wherein activating the user control comprises sliding a slide-bar coupled to the driving assembly of the surgical tool.

6. The method according to claim 5, wherein activating the user control comprises executing the distal-mode first and second phases of the distal advancement of the driving assembly in a single smooth distally-directed motion of the slide-bar.

7. The method according to claim 1, wherein the method further comprises, subsequently to the activating of the user control to distally advance the driving assembly, activating the user control to proximally retract the driving assembly, the proximal retraction having a proximal-mode first phase and a proximal-mode second phase,
    the proximal-mode first phase retracting the needle proximally into the surgical tool while the needle is rotationally stationary with respect to the longitudinal axis of the surgical tool, and
    the proximal-mode second phase rotating the needle in a second rotational direction opposite to the first rotational direction.

8. The method according to claim 7, wherein activating the user control comprises executing the proximal-mode first and second phases of the proximally-directed motion in a single smooth motion of the user control.

9. The method according to claim 7, wherein activating the user control comprises sliding a slide-bar coupled to the driving assembly of the surgical tool.

10. The method according to claim 9, wherein activating the user control comprises executing the proximal-mode first and second phases of the proximal retraction of the driving assembly in a single smooth proximally-directed motion of the slide-bar.

11. Apparatus comprising:
a surgical tool shaped to define a lumen and comprising a handle disposed at a proximal end of the surgical tool;
a driving assembly disposed within the handle and comprising proximal and distal portions, the proximal and distal portions being slidably coupled to each other; and
a needle slidably disposed within the lumen of the surgical tool and coupled to the proximal portion of the driving assembly such that (i) during distal advancement of the driving assembly with respect to the handle the needle is advanced distally within the lumen of the surgical tool, the needle being rotationally stationary with respect to a longitudinal axis of the surgical tool, and (ii) subsequently to the needle being advanced distally within the lumen of the surgical tool, distal advancement of the distal portion of the driving assembly with respect to the proximal portion of the driving assembly rotates the needle in a first rotational direction around the longitudinal axis of the surgical tool.

12. The apparatus according to claim 11, wherein (i) during proximal retraction of the driving assembly with respect to the handle the needle is retracted proximally within the lumen of the surgical tool, the needle being rotationally stationary with respect to the longitudinal axis of the surgical tool, and (ii) subsequently to the needle being retracted proximally within the lumen of the surgical tool, proximal retraction of the distal portion of the driving assembly with respect to the proximal portion of the driving assembly rotates the needle in a second rotational direction that is opposite to the first rotational direction.

13. The apparatus according to claim 11, wherein:
the proximal portion of the driving assembly is shaped to define a thread along at least a portion of the proximal portion,
the distal portion of the driving assembly is shaped to define a protrusion, and
the proximal and distal portions of the driving assembly are arranged such that (a) the protrusion and the thread engage with one another and (b) engagement between the protrusion and the thread as the distal portion of the driving assembly is advanced distally with respect to the proximal portion of the driving assembly rotates the needle in the first rotational direction around the longitudinal axis of the surgical tool.

14. The apparatus according to claim 11, wherein:
the proximal portion of the driving assembly is shaped to define a protrusion,
the distal portion of the driving assembly is shaped to define a thread along at least a portion of the distal portion, and
the proximal and distal portions of the driving assembly are arranged such that (a) the protrusion and the thread engage with one another and (b) engagement between the protrusion and the thread as the distal portion of the driving assembly is advanced distally with respect to the proximal portion of the driving assembly rotates the needle in the first rotational direction around the longitudinal axis of the surgical tool.

15. The apparatus according to claim 11, wherein:
the proximal portion of the driving assembly is shaped to define a first thread along at least a portion of the proximal portion,
the distal portion of the driving assembly is shaped to define a second thread along at least a portion of the distal portion, and
the proximal and distal portions of the driving assembly are arranged such that (a) the first and second threads engage one another, and (b) engagement between the first and second threads as the distal portion of the driving assembly is advanced distally with respect to the proximal portion of the driving assembly rotates the needle in the first rotational direction around the longitudinal axis of the surgical tool.

16. The apparatus according to claim 15, wherein engagement between the first and second threads as the distal portion of the driving assembly is retracted proximally with respect to the proximal portion of the driving assembly rotates the needle in the second rotational direction.

17. The apparatus according to claim 15, wherein:
the proximal portion of the driving assembly is shaped to define (a) an inner core, the first thread being around a distal length of the inner core, and (b) an outer surface surrounding a proximal length of the inner core, the outer surface being shaped to define a protrusion extending laterally with respect to the longitudinal axis of the surgical tool, and
the distal portion of the driving assembly comprises a hollow shaft element slidably coupled to the proximal portion of the driving assembly such that prior to distal advancement of the distal portion with respect to the proximal portion, the distal length of the inner core is disposed along the hollow shaft element.

18. The apparatus according to claim 17, wherein prior to distal advancement of the distal portion with respect to the proximal portion, the distal length of the inner core is disposed within the hollow shaft element, the second thread being on an inside surface of the hollow shaft element.

19. The apparatus according to claim 17, wherein:
the handle is shaped to define at least one protruding stop on an inner wall of the handle, and
the apparatus further comprises a user control coupled to the driving assembly and arranged such that a first activation of the user control (a) advances the driving assembly distally within the surgical tool such that (i) the needle is advanced distally within the lumen and (ii) the protrusion engages the at least one protruding stop to lock the proximal portion in place, and (b) subsequently advances the distal portion of the driving assembly distally with respect to the proximal portion of the driving assembly, wherein engagement between the first and second threads as the distal portion is advanced distally with respect to the proximal portion causes rotation of the proximal portion around the longitudinal axis of the surgical tool in the first directional rotation, thereby causing rotation of the needle in the first rotational direction.

20. The apparatus according to claim 19, wherein the user control is arranged such that a second activation of the user control (a) retracts the driving assembly proximally such that the needle is retracted proximally within the lumen and (b) subsequently retracts the distal portion of the driving assembly proximally with respect to the proximal portion of the driving assembly, wherein engagement of the first and second threads as the distal portion is retracted proximally with respect to the proximal direction causes rotation of the proximal portion around the longitudinal axis of the surgical tool in the second rotational direction, thereby causing rotation of the needle in the second rotational direction.

21. The apparatus according to claim 19, wherein the user control comprises a slide-bar coupled to the driving assembly and configured to be advanced by a user distally with respect to the handle to cause the first activation and to be retracted by the user proximally with respect to the handle to cause the second activation.

\* \* \* \* \*